United States Patent [19]

Marquarding et al.

[11] 4,442,029

[45] Apr. 10, 1984

[54] PROCESS FOR THE PREPARATION OF ACID AMIDES AND APPLICATION OF THE PROCESS

[76] Inventors: Dieter Marquarding, Darmstädter Strasse 11, 800 Munich 50; Helmut Aigner, Barerstrasse 52, 8000 Munich 40, both of Fed. Rep. of Germany

[21] Appl. No.: 460,881

[22] Filed: Jan. 25, 1983

Related U.S. Application Data

[63] Continuation of Ser. No. 198,251, Oct. 17, 1980, abandoned.

[30] Foreign Application Priority Data

Oct. 22, 1979 [DE] Fed. Rep. of Germany ....... 2942606

[51] Int. Cl.³ ............................................. C07C 102/04
[52] U.S. Cl. ............................... 260/112.5 R; 544/163; 564/139
[58] Field of Search ................... 564/139; 260/112.5 R

[56] References Cited

U.S. PATENT DOCUMENTS 3,933,783  1/1976  Yasuda et al. .............. 260/112.5 R

OTHER PUBLICATIONS

Wackerle "*Synthesis*", (3/79) 1979) pp. 197–198.
Aigner et al., "*Tetraheydron Letters*", No. 36 (1978) pp. 3325–3326.

*Primary Examiner*—Robert W. Ramsuer
*Attorney, Agent, or Firm*—Browdy & Neimark

[57] ABSTRACT

A process for the preparation of acid amides, comprising reacting a carboxylic acid and an amine in the presence of an isonitrile, wherein the isonitrile has at least one hetero-atom in the substituent present in the above-mentioned isonitrile group. The isonitrile is preferably morpholino-ethyl isocyanide, a new chemical compound.

1 Claim, No Drawings

PROCESS FOR THE PREPARATION OF ACID AMIDES AND APPLICATION OF THE PROCESS

This is a continuation, of application Ser. No. 198,251 filed Oct. 17, 1980 now abandoned.

The present invention relates to a process for the preparation of acid amides by reacting a carboxylic acid and an amine in the presence of an isonitrile, and application of this process.

Numerous processes are known for the preparation of amides from carboxylic acids and amines. Amide syntheses are of particular importance in the preparation of peptides and pharmaceutically active systems which contain amide groups.

In the field of peptide synthesis the so-called carbodiimide method for linking amide bonds has gained great importance. This process, however, contains in part serious disadvantages. In the first place the urea derivative which is regularly formed from the carbodiimide in the reaction is frequently extremely difficult to separate from the desired reaction product. In the case of several of these urea derivatives a carcinogenic effect has also been demonstrated. In addition, unwanted secondary reactions take place to a great extent, which lead inter alia to the formation of N-acyl ureas. The separation of these by-products which adversely affect the yield is also subject to somewhat serious problems.

The synthesis of amides from carboxylic acids and amines in the presence of isocyanides has been described by the applicants in Tetrahedron Letters, No. 36, pages 3325 to 3326 (1978). In addition, a report in "Synthesis", March 1979, pages 197 to 198, relates to such acid amide formation and its application to peptide synthesis. In the amidations described above various aliphatic and cycloaliphatic isonitriles were used as activating agents. The yields which are obtainable are, however, still unsatisfactory, in particular in the case of the synthesis of peptide systems which are somewhat difficult to synthesize.

The object of the present invention is to provide a process for amidation which will permit the synthesis of amides, in particular peptides, and also other amide systems with pharmaceutical effect in high yields and without racemization, in which the desired amides may be obtained from the reaction mixture in a simple manner. Furthermore such a process should permit the formation of amide systems in high yields which cannot be synthesized with satisfactory yields according to conventional processes and in particular according to the known carbodiimide method.

The present invention provides a process for the preparation of acid amides by reacting a carboxylic acid and an amine in the presence of an isonitrile, wherein the isonitrile has at least one hetero-atom in the substituent present in the isonitrile group.

The process according to the invention may suitably find application in the synthesis of peptides, or in the amidation of penicillin or cephalosporin derivatives.

By using isonitriles with at least one heteroatom in the substituent present in the isonitrile group as an activating and dehydrating agent, acid amides and in particular even peptide systems which are difficult to obtain may be produced in a simple manner in unexpectedly high yields. This is particularly unexpected since, when preparing known peptide systems by using modified carbodiimides, for example when introducing carbodiimides with tertiary amino groups, it is not generally possible to increase the peptide yields. Thus the conventional carbodiimides, which incidentally are not directly comparable with the isonitriles for various reasons, display no tendency, on the insertion of heteroradicals, to a greater reactivity which would be desirable in particular in the synthesis of peptides which are difficult to obtain. In addition, carbodiimides modified in this way have not, incidentally, been extensively adopted in practice, partly because they are difficult to obtain and partly on account of other secondary reactions etc.

According to a preferred embodiment of the process according to the invention, those isonitriles are used whose hetero-atom has a free pair of electrons. It is speculated that this facilitates protonation of the hetero-atom, which could promote the protonation of the isonitrile function as an interimmediate stage.

With the process according to the invention, particularly favourable results are obtained with isonitriles in which the hetero-atom in the substituent in the isonitrile group and the C atom of the functional isonitrile group are in a 1,5 or 1,6 position relative to one another.

For example, an N, S, O or P atom or combinations thereof in an appropriate bond may occur as the hetero-atom. Amongst these compounds the N atom in particular is preferred as the hetero-atom. Especially favourable yields are obtained in particular with N-heterocyclic-substituted isonitriles. Isonitriles, in which the hetero compound contains electron-displacing groups or substituents, e.g. methyl or allyl groups, are also particularly suitable for use according to the invention.

In addition, the basic isonitriles of the type described provide the possibility of very easy separation of the formamides formed as an accompanying product, and therefore such basic isonitriles are particularly preferred.

Typical examples of the isonitriles used according to the invention for amidation are:

Isonitriles:

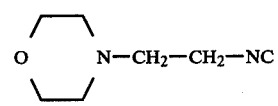 MAI

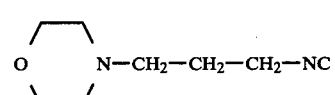 MPI

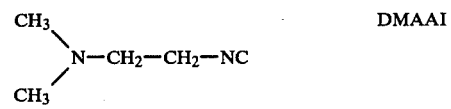 DMAAI

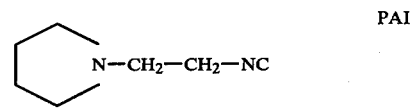 PAI

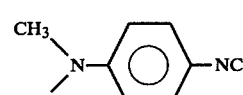

-continued
Isonitriles:

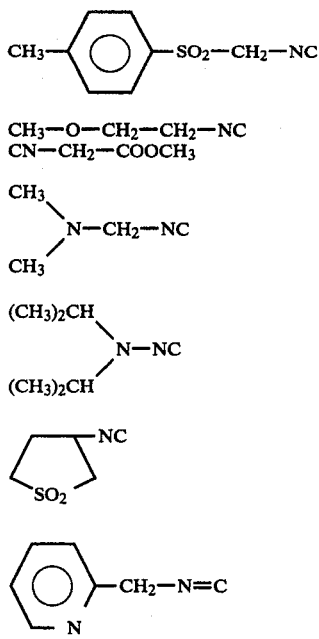

Most of the compounds indicated above are known in the literature, and so their synthesis may easily be carried out in accordance with the processes disclosed therein. One exception among them, however, is morpolino-ethyl-isocyanide (MAI), which may be obtained, taking 2-(4'-morpholinyl)-ethylamine as the starting material, by the phosgene method known in the preparation of isonitriles. This new compound, the use of which is particularly preferred in the process according to the invention, has a boiling point at 0.05 torr of B 70° C. and a density at room temperature of 1.014. With respect to the synthesis methodology which may generally be applied, reference is made to "Angewandte Chemie" (Applied Chemistry), vol. 77, 1965/No. 11.

The course of the amidation process according to the invention may be clearly seen in the reaction scheme below.

REACTION SCHEME $R_S$—COOH + $R_I$—NC $\longrightarrow$

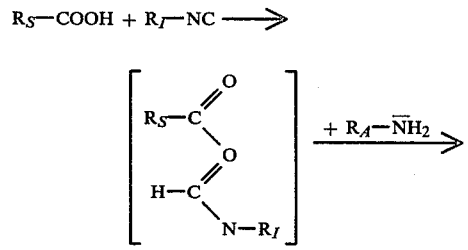

-continued
REACTION SCHEME $R_S$—CO—NH—$R_A$ + $R_I$—NH—CHO $R_S$=acid residue (in peptides N-terminal protected amino acid or peptide residue)
$R_I$=substituent of isonitrile with hetero-atom
$R_A$=amine residue (in peptides C-terminal protected amino acid or peptide residue)

The amide may be prepared in a suitable protonic or aprotic solvent. Such solvents are, for example, isopropanol, dichloromethane, chloroform, carbon tetrachloride, ethyl acetate, dimethyl formamide etc. The reaction usually takes place at room temperature and is over very quickly. Only in the case of systems which are difficult to obtain and which to a certain extent cannot be produced at all according to the conventional carbodiimide methodology, was a reaction at a somewhat elevated temperature necessary.

The particular application of the process according to the invention lies in the mild preparation of amide bonds. It may be employed particularly advantageously for preparing peptides. In this case the procedure indicated below may generally be followed:

Procedure 2.5 mmole of the amine component, if possible as a hydrochloride, together with 2.5 mmole of triethylamine are added to a solution of 2.5 mmole of the acid component (together with 5 mmole of hydroxysuccinimide) and 2.5 to 3 mmole of isonitrile in a suitable solvent (e.g. dichloromethane, ethyl acetate, dioxane, isopropanol, dimethyl formamide) over 30 minutes. The reaction mixture is stirred for approximately 4 hours, for example at room temperature. It is then concentrated in a vacuum, the residue is absorbed, for example in ethyl acetate, and it is then shaken out twice with a weak acid, e.g. 1 N-hydrochloric acid or citric acid solution, then twice with (for example 7.5%) sodium bicarbonate solution and finally twice with water. The organic phase is dried by sodium sulphate. The product is obtained after complete evaporation of the solvent in a vacuum, usually in an analytically pure form.

If no basic function is present in the isonitrile starting component, the formamide derivate which is produced is removed by distillation or even recrystallization.

It is clear from the above procedure that in many cases it is advantageous—although not always necessary—additionally to add 2 mmole of N-hydroxysuccinimide per mole of the acid component of the reaction. In this way, as in the case of the known synthesis of carbodiimide, a high degree of freedom from racemization is obtained.

The following amide derivates, which predominantly represent peptides, are prepared according to this procedure:

| Product | Solvent | isonitrile | yield % | f.p. °C. | analysis C | H | N | remarks |
|---|---|---|---|---|---|---|---|---|
| benzoic acid benzylamide | CH2Cl2 | MAI | 69 | 106 | | | | Duration of reaction 3 days |
| Z—Val—Gly—OMe | CH2Cl2 | MAI | 80 | 157–158 | c. 59,62 f. 59,72 | 6,88 6,86 | 8,69 8,67 | |
| Z—Val—Gly—OMe | Ethyl | MAI | 81 | 156–158 | c. 59,62 | 6,88 | 8,69 | |

-continued

| Product | Solvent | isonitrile | yield % | f.p. °C. | C | H | N | remarks |
|---|---|---|---|---|---|---|---|---|
| Z—Val—Val—OMe | acetate CH$_2$Cl$_2$ | MAI | 90 | 98–100 | f. 59,58<br>c. 62,62<br>f. 62,74 | 6,93<br>7,74<br>7,58 | 8,69<br>7,69<br>7,81 | moment of rotation of product |
| Z—Val—Val—OBtu | CH$_2$Cl$_2$ | MAI | 91 | solid | | | | $[\alpha]_D^{20}$ — 32,5<br>c = 0,4 EtOH |
| Z—Leu—Gly—OEt | CH$_2$Cl$_2$ | MAI | 90 | 98–100 | | | | |
| Z—Leu—Leu—OMe | CH$_2$Cl$_2$ | MAI | 94 | 79–81 | | | | |
| Z—Ala—Phe—OMe | CH$_2$Cl$_2$ | MAI | 94 | 96–97 | c. 65,61<br>f. 65,49 | 6,29<br>6,16 | 7,29<br>7,39 | |
| Z—Ala—Pro—OMe | CH$_2$Cl$_2$ | MAI | 87 | oil | c. 61,03<br>f. 60,96 | 6,64<br>6,61 | 8,39<br>8,26 | duration of reaction 7 days/40° C. |
| Boc—Aib—Aib—OMe | CH$_2$Cl$_2$ | MAI | 68 | | | | | |
| TFA—Phe—Gly—OMe | CH$_2$Cl$_2$ | MAI | 77 | 118–121 | | | | |
| TFA—Phe—Phe—OMe | CH$_2$Cl$_2$ | MAI | 76 | 174–176 | | | | |
| Boc—Gly—Ala—Val—OMe* | CH$_2$Cl$_2$ | MAI | 90 | 104–106 | c. 53,47<br>f. 53,37 | 8,13<br>7,87 | 11,69<br>11,75 | without Hosu** |
| Boc—Gly—Ala—Val—OtBu* | CH$_2$Cl$_2$ | MAI | 96 | 106–108 | | | | |
| Z—Ala—GlyOMe | CH$_2$Cl$_2$ | DMAAI | 68 | 92–94 | | | | |
| Z—Val—GlyOMe | CH$_2$Cl$_2$ | DMAAI | 62 | 155–156 | | | | |
| Z—Ala—GlyOMe | CH$_2$Cl$_2$ | PAI | 61 | 91–94 | | | | |
| Z—Ala—GlyOMe | CH$_2$Cl$_2$ | CN—CH$_2$—COOMe | 75 | 90–92 | | | | recrystallized |
| Z—Ala—GlyOMe | CH$_2$Cl$_2$ | CH$_3$—⟨O⟩—SO$_2$—CH$_2$—NC | 60 | 153–155 | | | | recrystallized |
| Z—Val—GlyOMe | CH$_2$Cl$_2$ | (CH$_3$)$_2$—N—⟨O⟩—NC | 67 | 150–152 | | | | recrystallized/ without Hosu |
| Bz—Val—GlyOMe | Iso-propanol | MPI | 80 | | c. 63,73<br>f. 63,86 | 7,55<br>7,72 | 8,74<br>8,85 | without Hosu/ recrystallized |
| Z—Val—GlyOMe | Aceto-nitrile | MPI | 61 | 156–158 | | | | | c. = calculated
f. = found
*Boc—Gly—Ala—OH. as acid component
**Hosu = Hydroxy-succinimide The identification of the reaction product formed is made, if no microanalysis values are indicated, by conventional spectroscopic methodology. The yield values given have not yet been optimized and so could be increased still further with respect to the values which are in part quite high. The table shows that even peptide systems which are somewhat difficult to obtain may be obtained in a high yield.

Preparation of MAI

1st. Stage

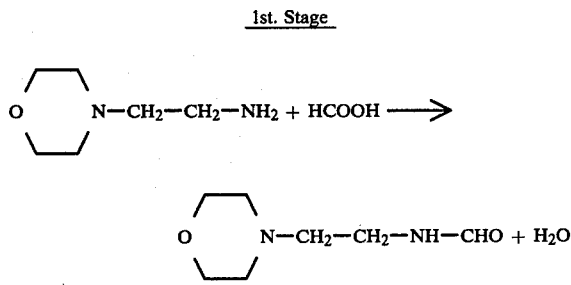

0.7 mole of amine and 30 ml of formic acid in 300 ml of toluene are heated to boiling on a water separator. When the reaction water is distilled off the mixture is concentrated in a vacuum and subsequently absorbed in dichloromethane. Ammonia is added to the solution until saturation, and the latter is filtered and again concentrated in a vacuum. The residue is distilled in a high vacuum.

Boiling point 110° C. 0.05 torr

H-NMR: —CHO ppm ($\delta$)=8.0 (s) TMS as internal standard

IR: C=O 1670 cm$^{-1}$

2nd. Stage

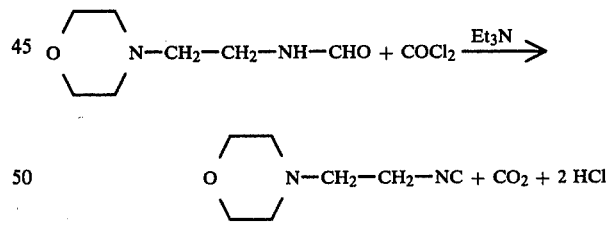

1 mole of 2-morpholino-ethyl formamide, 320 ml of triethyl amine and 450 ml of dichloromethane are the starting materials. 1 mole of phosgene is introduced while stirring and cooling with ice. The mixture is allowed to reach room temperature and is stirred for 3 hours. Within 1 hour 40 g of ammonia is introduced (until saturation) while cooling with ice, and the mixture is filtered and concentrated. The residue is distilled in a high vacuum.

Boiling point 70° C. 0.05 torr

IR: isonitrile bands: 2160 cm$^{-1}$

The preparation of MAI with electron-displacing groups in the morpholino radical is carried out in a similar manner by appropriate selection of the starting amine.

I claim:

1. In a process for the preparation of acid amides by reacting a carboxylic acid and an amine in the presence of an isonitrile, the improvement consisting of using as said isonitrile a compound selected from the group consisting of:
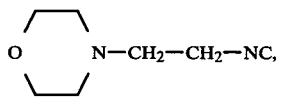
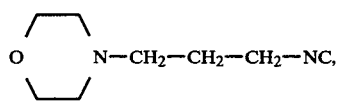
-continued
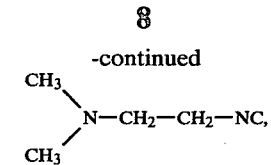
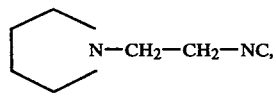
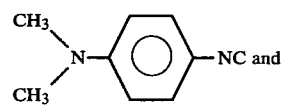
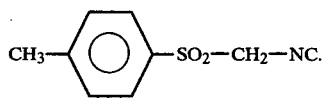
* * * * *